(12) United States Patent
Umasankar et al.

(10) Patent No.: US 9,816,959 B2
(45) Date of Patent: Nov. 14, 2017

(54) SENSOR FOR MONITORING OF ETHANOL

(71) Applicants: Yogeswaran Umasankar, Miami, FL (US); Shekhar Bhansali, Weston, FL (US)

(72) Inventors: Yogeswaran Umasankar, Miami, FL (US); Shekhar Bhansali, Weston, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 101 days.

(21) Appl. No.: 14/982,897

(22) Filed: Dec. 29, 2015

(65) Prior Publication Data

US 2017/0184537 A1   Jun. 29, 2017

(51) Int. Cl.
G01N 27/403   (2006.01)
G01N 27/407   (2006.01)
G01N 27/30    (2006.01)
G01N 27/333   (2006.01)
G01N 27/406   (2006.01)
(Continued)

(52) U.S. Cl.
CPC ....... *G01N 27/4074* (2013.01); *A61B 5/6801* (2013.01); *G01N 27/301* (2013.01); *G01N 27/3335* (2013.01); *G01N 27/403* (2013.01); *G01N 27/4065* (2013.01); *G01N 27/4163* (2013.01); *G01N 33/006* (2013.01); *G01N 33/48707* (2013.01); *G01N 33/4972* (2013.01); *A61B 5/681* (2013.01); *A61B 2010/0009* (2013.01); *G01N 33/0047* (2013.01)

(58) Field of Classification Search
CPC .......... A61B 2010/0009; A61B 5/4845; A61B 5/6801; A61B 5/681; A61B 5/1486; A61B 5/1477; G01N 27/403; G01N 33/0047; G01N 33/006
See application file for complete search history.

(56) References Cited

U.S. PATENT DOCUMENTS 5,944,661 A  * 8/1999 Swette ............... A61B 10/0064
                                        204/403.06
2006/0272943 A1   12/2006 Chien et al.
(Continued)

FOREIGN PATENT DOCUMENTS

JP    2009-294045 A  * 12/2009  ............. G01N 33/98

OTHER PUBLICATIONS

JPO computer-generated Englsih language transalation of Yofu et al. JP 2009-294045 A, downloaded Jun. 26, 2017.*
(Continued)

*Primary Examiner* — Alexander Noguerola
(74) *Attorney, Agent, or Firm* — Soliwanchik, Lloyd & Eisenschenk

(57) ABSTRACT

The subject invention provides devices, and methods of making and using the same, for the non-invasive detection of ethanol in a sample. In specific embodiments, the fuel cell based ethanol detector of the subject invention is capable of measuring the concentration of ethanol vapor in the presence of water vapor, which is known to confound signal readings in conventional detectors. Advantageously, the electrochemical sensors provided herein are highly stable and accurate, especially suitable for low-cost, continuous monitoring of ethanol content in transdermal perspiration samples.

20 Claims, 15 Drawing Sheets

(51) Int. Cl.
| | |
|---|---|
| G01N 27/416 | (2006.01) |
| G01N 33/497 | (2006.01) |
| G01N 33/487 | (2006.01) |
| G01N 33/00 | (2006.01) |
| A61B 5/00 | (2006.01) |
| A61B 10/00 | (2006.01) |

(56) References Cited

U.S. PATENT DOCUMENTS

2009/0182216 A1* 7/2009 Roushey, III ...... A61B 5/14546
600/364
2013/0104624 A1 5/2013 Devine

OTHER PUBLICATIONS

An, Tae Kyu et al., "Synthesis and characterization of an ester-terminated organic semiconductor for ethanol vapor detection," *Organic Electronics*, 2014, 15:2277-2284.
Anderson, Joseph C. et al., "The kinetics of transdermal ethanol exchange," *J. Appl Physiol*, 2006, 100:649-655.
Izquierdo, J. et al., "Imaging Local Surface Reactivity on Stainless Steels 304 and 316 in Acid Chloride Solution using Scanning Electrochemical Microscopy and the Scanning Vibrating Electrode Technique," *Electrochimica Acta*, 2014, 134:167-175.
Jeng, King-Tsai etal., "A versatile electrochemical fuel sensor for direct membrane fuel cell applications," *Sensors and Actuators B*, 2007, 125:278-283.
Jiang, Luhua et al., "Development of Air-Breating Direct Ethanol Fuel Cells With PtSn As Anode," *Prepr. Pap.-Am. Chem. Soc., Div. Fuel Chem.*, 2004, 49(2):668-670.
Kadir, Rosmalini Ab et al., "Nb2O5 Schottky based ethanol vapour sensors: Effect of metallic catalysts," *Sensors and Actuators B: Chemical*, 2014, 202:74-82.
Kim, Hyo-Joong et al., "Highly sensitive and selective gas sensors using p-type oxide semiconductors: Overview," *Sensors and Actuators B: Chemical*, 2014, 192:607-627.
Kim, Ki-Chul et al., "Detection of ethanol gas concentration by fuel cell sensors fabricated using a solid polymer electrolyte," *Sensors and Actuators B*, 2000, 67:194-198.
Sanford, Caryn L. et al., "Determination of Ethanol in Alcohol Samples Using a Modular Raman Spectrometer," *Journal of Chemical Education*, Sep. 2001, 78(9):1221-1225.
Scram Systems. "Alcohol Monitoring Systems, Inc.", *Giner Inc.*, 2016, accessed from: http://www.scramsystems.com/
Shabaneh, A.A. et al., "Reflectance response of tapered optical fiber coated with graphene oxide nanostructured thin film for aqueous ethanol sensing," *Optics Communications*, 2014, 331:320-324.
Yu, Ming-Ru et al., "Performance evaluation of ZnO-CuO hetero junction solid state room temperature ethanol sensor," *Mat. Res. Bulletin*, 2012, 47:1713-1718.

* cited by examiner

Top view

Lateral view

Dorsal view

Working prototype

SENSOR FOR MONITORING OF ETHANOL

This invention was made with government support under contract number 1444327 awarded by the National Science Foundation and under contract number 110483 awarded by the National Science Foundation. The government has certain rights in the invention.

BACKGROUND OF INVENTION

Alcohol is eliminated from the body by two mechanisms: metabolism and excretion. Metabolism accounts for the removal of greater than 90% of the alcohol consumed, removing it from the body via oxidation of the ethyl alcohol molecule to carbon dioxide and water primarily in the liver. The remaining alcohol is excreted unchanged wherever water is removed from the body, breath, urine, perspiration, and saliva.

Although excretion accounts for less than 10% of the eliminated alcohol, it is significant because unaltered alcohol excretion permits an accurate measurement of alcohol concentration in the body by way of both breath analysis and insensible skin perspiration. Insensible skin perspiration is the vapor that escapes through the skin through sweating. This insensible skin perspiration can be used to obtain a transdermal measurement estimating a measure of blood alcohol concentration (BAC), referred to as transdermal alcohol concentration (TAC).

A survey of literature reveals that there are no reports available for continuously monitoring TAC through transdermal diffusion or perspiration, because the pharmacokinetic process of alcohol is complex owing to the intricate nature of its distribution into the various tissues of the body. The balance between absorption and elimination of alcohol is reflected in the BAC, which continues to rise until absorption is complete. After a maximum value is reached, the BAC begins to decrease during the elimination phase primarily due to the metabolism process in the liver as well as through transdermal diffusion.

A number of ethanol sensors have been developed for monitoring driving under the influence (DUI) offenders. The types of ethanol sensors include, for example, spectrophotometers, semiconductor sensors, and fuel cell sensors. Among these, the principle behind spectroscopic sensors involves the measurement of changes in light wavelength and intensity in the presence of ethanol. The semiconductor sensor monitors changes in resistance due to changes in ethanol concentration. The fuel cell sensor monitors the oxidation of ethanol at the anode while reducing the atmospheric oxygen at the cathode. The fuel cell sensor has high specificity, accuracy, calibration stability and long working life compared to the other two types of sensors. However, these sensors all suffer from high interference caused by humidity and cannot be used for continuous monitoring. One example of a widely used ethanol sensor is the breathalyzer, which is incapable of continuously monitoring ethanol concentration in DUI offenders.

Therefore, there still remains a need for stable and selective ethanol sensors that are effective in a humid environment.

BRIEF SUMMARY

The subject invention provides devices, and methods of making and using the same, for the non-invasive detection of ethanol. In specific embodiments, the fuel cell based ethanol detector of the subject invention is capable of measuring the concentration of ethanol vapor in the presence of water vapor, which is known to confound signal readings in conventional detectors.

Advantageously, the electrochemical sensors provided herein are highly stable and accurate, and especially well-suited for low-cost, continuous monitoring of ethanol content in transdermal perspiration samples.

In one aspect, the subject invention provides a fuel cell based device for continuously detecting the concentration of ethanol vapor in a sample, wherein the device comprises:
  a sensor unit comprising a working electrode as an anode, a counter electrode as a cathode, a reference electrode, and a polymer electrolyte membrane, the anode and the cathode being separated by, and respectively in electrical contact with, the electrolyte, the reference electrode being in electrical contact with the electrolyte and disposed adjacent to, though separated from, the counter electrode;
  circuitry capable of controlling the potential applied to the sensor unit; and
  circuitry capable of measuring the current output of the sensor unit;
  wherein the sensor is capable of separating signals produced by ethanol from those produced by background humidity.

In some embodiments, the electrolyte material is a proton exchange membrane (PEM). In a preferred embodiment, the electrolyte is NAFION®, a class of perfluorinated PEM.

In some embodiments, the sample is a product of a human transdermal diffusion process. Exemplary embodiments provide that the sample is human skin perspiration.

In a specific embodiment, the electrodes comprise a material selected from iron, gold, nickel, platinum, carbon, and one or more of these materials combined as a catalyst.

In another aspect, the subject invention provides a method of detecting the concentration of ethanol vapor in a skin perspiration sample collected from a human subject, wherein the method comprises:
  contacting a sample, with the sensing device provided herein;
  obtaining and storing the open-circuit potential (OCP) of the sensor unit by scanning a first range of voltage across the sensor;
  comparing the OCP to a threshold value characteristic to the material employed in the working electrode; and
  applying the OCP across the working and the reference electrodes while conducting a series of amperometric measurements;
  wherein,
  if the OCP is less than the threshold value, the amperometric data are fitted against a pre-determined calibration curve to remove the signals arising from humidity in the surrounding environment and the concentration of ethanol is subsequently determined; and
  if the OCP is greater than the threshold value, the concentration of ethanol is directly determined based on the amperometric data.

In some embodiments, the device is placed in direct contact with the skin surface of the subject.

In certain embodiments, the device can measure the concentration of ethanol in the presence of humidity by fitting the measured amperometric data to a pre-determined calibration curve.

In yet another aspect, the subject invention provides a device for determining blood alcohol content (BAC) based on a skin perspiration sample collected from a human subject, comprising:

the fuel cell based sensing device provided herein;
a means of displaying the ethanol concentration measured with the sensing device; and
circuitry capable of processing and analyzing the ethanol concentration data output by the sensing device.

In some embodiments, the device optionally comprises an electronic platform for receiving user input.

The casing can be selected as described herein in accordance with the desired application for which the device is designed.

Advantageously, the electrochemical sensor provided herein can be integrated into a wearable device for convenient and accurate detection of ethanol levels.

DETAILED DISCLOSURE

Figure 1A:
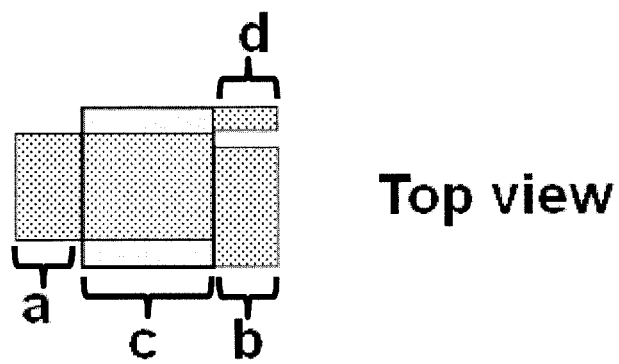
FIG. 1A is a top view of a preferred embodiment of the ethanol sensor.

The subject invention provides devices, and methods of making and using the same, for the non-invasive detection of ethanol. In specific embodiments, the fuel cell based ethanol detector is capable of measuring the concentration of ethanol vapor in the presence of water vapor, which is known to confound signal readings in conventional detectors. Advantageously, the electrochemical sensors provided herein are highly stable and accurate, and are especially well-suited for low-cost, continuous monitoring of ethanol content in transdermal perspiration samples.

In one aspect, the subject invention provides a fuel cell based device for detecting the concentration of ethanol vapor in a sample, comprising:
a sensor unit comprising a working electrode as the anode, a counter electrode as the cathode, a reference electrode, and a polymer-based membrane electrolyte, the anode and the cathode being separated by, and respectively in electrical contact with, the electrolyte, the reference electrode being in electrical contact with the electrolyte and disposed adjacent to, though separated from, the counter electrode;
circuitry capable of controlling the potential applied to the sensor unit; and
circuitry capable of measuring the current output of the sensor unit;
wherein the sensor is capable of separating signals produced by ethanol from those produced by background humidity.

In some embodiments, the electrolyte material is a proton exchange membrane (PEM). In a preferred embodiment, the electrolyte is NAFION® (DuPont), a class of perfluorinated PEM.

A PEM-based fuel cell operates with gaseous hydrogen as fuel and oxygen from the air as the oxidant. In conventional PEM-based fuel cells, the PEM comprises one or more fluorinated polymers. It is desirable to employ PEMs with high proton conductivity at low relative humidity, and long-term chemical, electrochemical, and thermal stability, as well as low gas permeability under normal operating conditions. In addition to NAFION®, other organic polymer membranes can also be used in the fuel cell based sensor as the electrolyte. Non-limiting examples include GORE-SELECT® reinforced membranes (W. L. Gore), ACIPLEX® (Asahi Chemicals), FLEMION® (Asahi Glass), and BAM® (Ballard Power) for cell operation temperature not exceeding 90° C.; other art-recognized sulfonated or phosphonated polymers can be used in high-temperature applications In some embodiments, the working electrode is located on the anode side of the membrane, and the counter and reference electrodes are placed on the cathode side of the membrane (FIGS. 1A-1D). The active surface area of the working electrode can be designed to be slightly less than that of the counter electrode for the purpose of maximizing the extent of oxygen reduction at the counter electrode and providing sufficient oxygen supply to consume the fuel at the working electrode/PEM interface.

In contrast to traditional fuel cells, which employ a two-electrode system, i.e., an anode and a cathode, an embodiment of the subject invention employs a three-electrode system. The three-electrode system is advantageous because, in a two-electrode system, the electrochemical potential measurement reflects the full-cell reaction potential, whereas in the three-electrode system the half-cell potential can be measured independently. A sensor previously reported in U.S. Pat. No. 5,944,611 by Swette et al. also employs a three-electrode system, but the system relies on the full-cell reaction potential to delineate the concentration of ethanol.

Figure 1B:
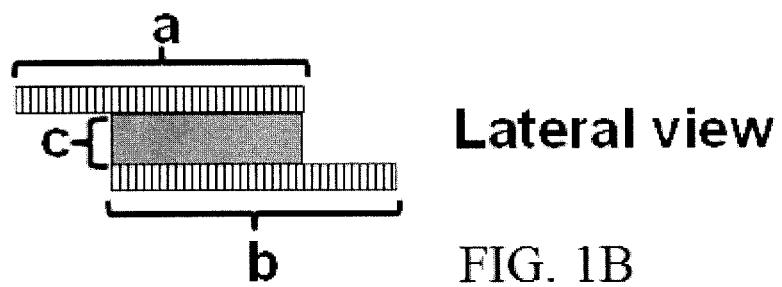
FIG. 1B is a lateral view of a preferred embodiment of the sensor.
Figure 1C:
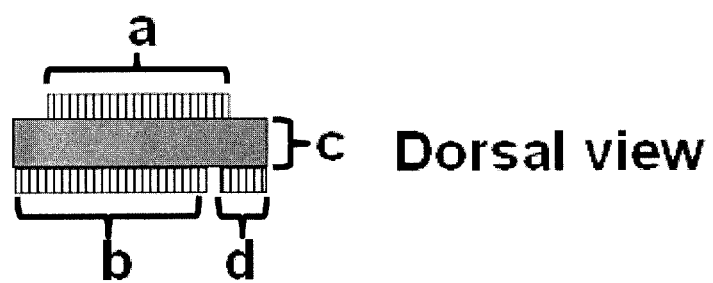
FIG. 1C is a dorsal view of a preferred embodiment of the sensor.
Figure 1D:
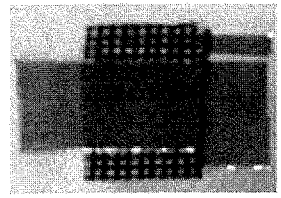
FIG. 1D shows a working prototype of a preferred embodiment of the sensor.

In some embodiments of the subject invention, the three-electrode system can be constructed in such a way that the working electrode and the reference electrode are located in close proximity to each other, albeit on opposite sides of the PEM electrolyte, enabling easy exchange of $H^+$ ions (FIGS. 1A and 1B). This design facilitates the monitoring of the anodic reaction of the fuel cell based sensor.

Other advantages of this design include, but are not limited to, a stable reference voltage resulting from using atmospheric oxygen reduction potential as the reference voltage across the reference electrode and the working electrode, prevention of short circuit voltage between the working electrode and the reference electrode, and increase in electron flow with increased electrode surface area.

Figure 3:
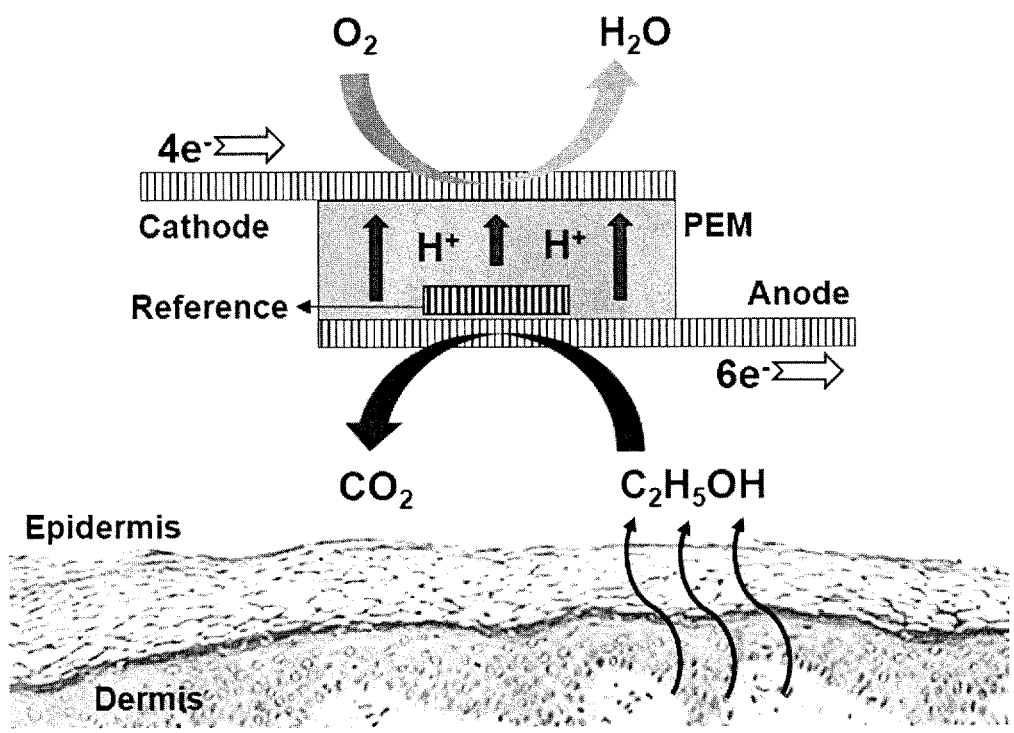
FIG. 3 is a schematic showing the mechanism of a fuel cell based sensor for continuous monitoring of ethanol in close proximity with the epidermal layer.

If water vapor is present in the sample, the humidified ethanol vapor gets oxidized at the anode to form protons, electrons, and carbon dioxide. During this electrochemical reaction, the protons are exchanged to the cathode through the PEM. Simultaneously, the atmospheric oxygen gets reduced to water in the presence of protons and electrons. A schematic of the reaction and the mechanism of the fuel cell based ethanol sensor are given in FIG. 3 and Equations (1) and (2), respectively. The anode and cathode in FIG. 3 represent the working and the counter electrode, respectively:

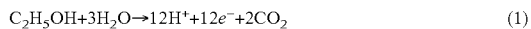

$$C_2H_5OH + 3H_2O \rightarrow 12H^+ + 12e^- + 2CO_2 \quad (1)$$

$$3O_2 + 12H^+ + 12e^- \rightarrow 6H_2O \quad (2)$$

$$C_2H_5OH + 3O_2 \rightarrow 3H_2O + 2CO_2 \quad (3).$$

Figure 4:
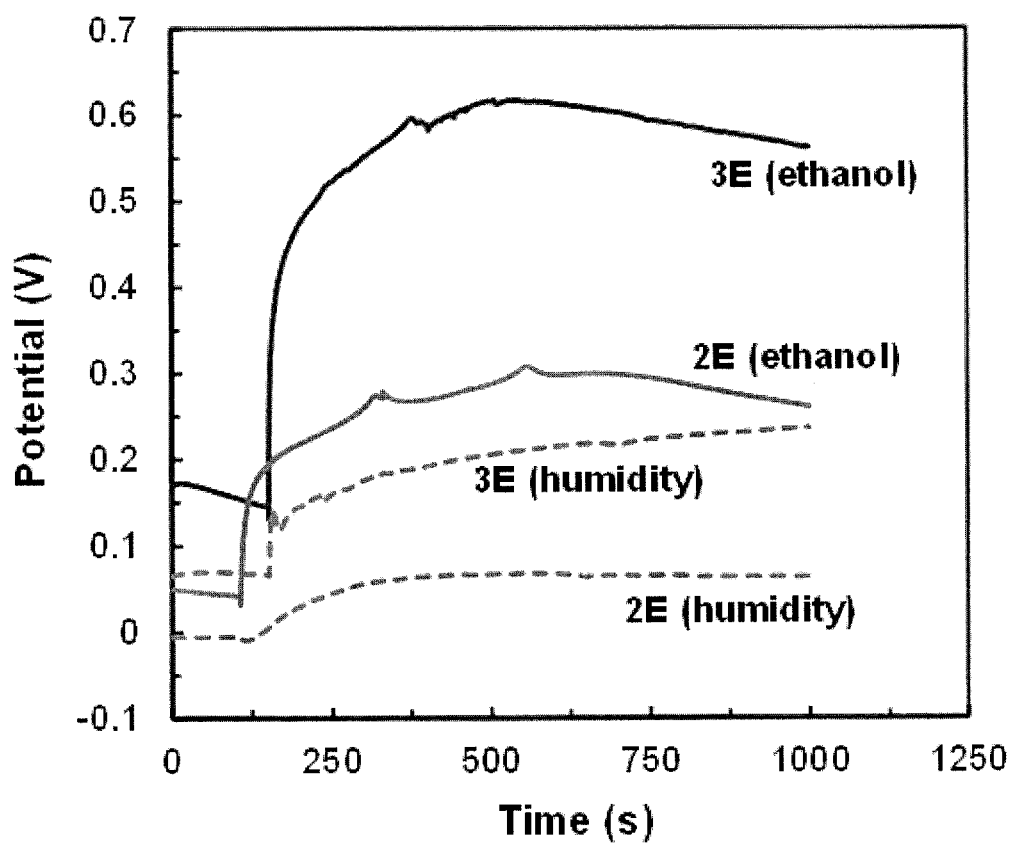
FIG. 4 shows the comparison in OCP measurements of ethanol and humidity, respectively, between a two-electrode system (2E) and a three-electrode system (3E), both employing stainless steel as the catalyst on the electrodes.

In a traditional two-cell system, the measured potential is that of the full-cell reaction as given in Equation (3). The full-cell reaction, however, is often interfered with by the cathodic reaction, where the byproduct water affects both the current and the potential output of the sensor when the background humidity is higher than the usual operating condition. This phenomenon has been demonstrated using OCP experiments as shown in FIG. 4, where a three-electrode system outputs 0.6 V in the presence of ethanol. The same Figure shows that the OCP voltage of the two-electrode system is significantly lower than that of the three-electrode system. This lowered OCP can be attributed to the influence of oxygen reduction reaction signal from the cathode side. In some embodiments, the three-electrode system also provides a wider potential window between the ethanol and the humidity signals when compared to the two-electrode system. Therefore, the three-electrode system has been adapted to eliminate signal interference.

One advantage of the three-electrode system is that it monitors only the anodic half-cell reaction as given in Equation (1). This can be achieved by measuring the potential between the anode and the reference electrode, and letting the current pass between the anode and the cathode. This mechanism yields a more stable signal of the ethanol oxidation at the anode than the traditional two-electrode system.

In some embodiments, the sample is a product of human transdermal diffusion process. Exemplary embodiments provide that the sample is obtained from human skin perspiration.

In a specific embodiment, the electrodes comprise a material selected from iron, gold, nickel, platinum, carbon, and one or more of these material combined as a catalyst. In some embodiments, the electrodes comprise flexible materials deposited with a thin layer of catalysts provided therein.

Figure 5:
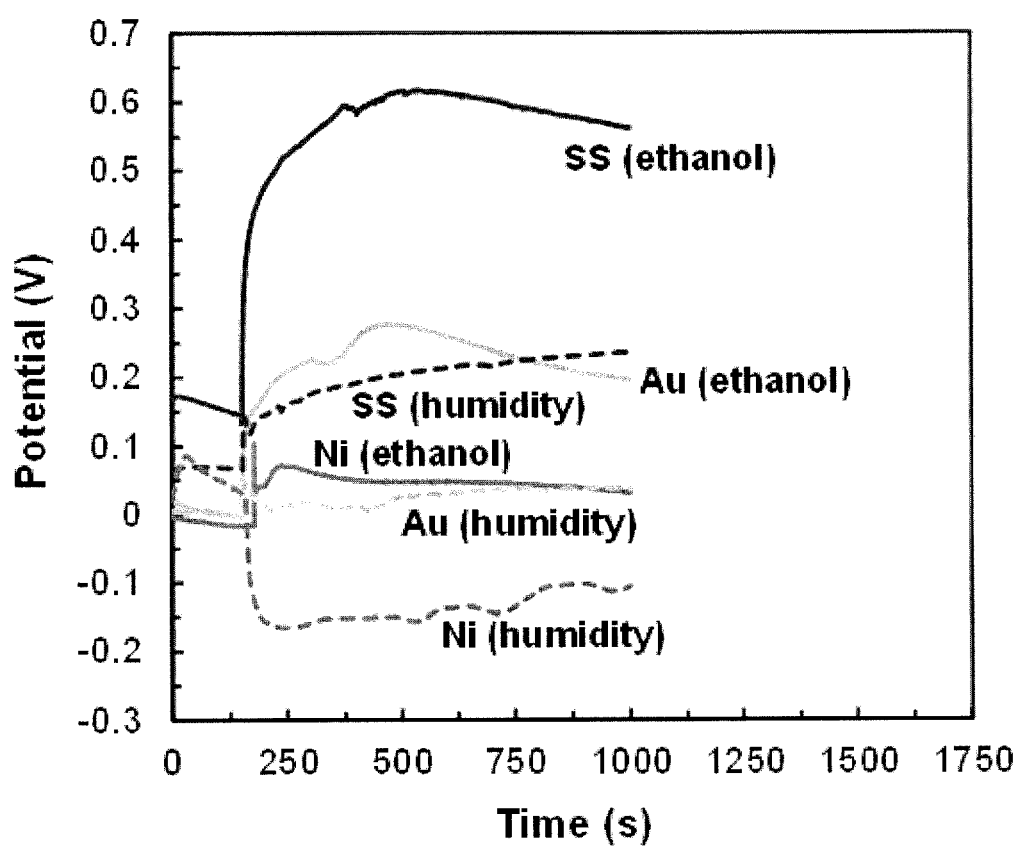
FIG. 5 shows the OCP signals for ethanol and humidity, respectively, for three different metallic catalysts: stainless steel, nickel, and gold.

Preferably, the working electrode comprises stainless steel while the counter electrode comprises nickel. As shown in FIG. 5, the potential for ethanol reduction (preferably at 0.6 V) and for oxygen reduction (preferably at −0.2 V) have been observed on electrodes comprising stainless steel and nickel, respectively, making them the preferred materials for the construction of the fuel cell sensor. Advantageously, the fuel cell based sensor constructed from stainless steel and nickel electrodes not only demonstrates efficacy in providing selective sensing capability for ethanol but also lowers the overall cost of the sensor.

It has been observed that the ethanol curves measured by OCP techniques deviate in the presence of humidity, making it difficult to obtain an accurate linear range (calibration curve) for the sensor. This humidity gradient affects various factors including the rate of $H^+$ transfer, thus the pH, through the electrolyte membrane, the amount of ethanol that is oxidized at the anode, and the amount of oxygen that gets reduced at the cathode. Together, these factors affect both the full cell potential ($E_{cell}$) value and the current signal generated. Deriving the relationship between signals generated from humidity and ethanol is challenging, because in a sandwiched fuel cell setup there will be a humidity gradient between the outer layers and the middle layer.

In a preferred embodiment of the subject invention, an amperometric technique is used to minimize humidity interference. In general, an amperometric technique provides a current signal generated between the working and counter electrodes during the fuel cell reaction when a potential is applied between the working and reference electrode. By keeping the electrode potential exactly at the full-cell potential ($E_{cell}$) at any given humidity level, the current flow due to humidity can be eliminated.

In some embodiments, the fuel cell based ethanol sensor further comprises a thin coating of an ethanol-permeable membrane around the anode while the cathode is left open to allow full access to atmospheric oxygen. This membrane coating prevents the anode from contacting other compounds, and allows the transfer of ethanol from the surrounding area to the electrode surface. Advantageously, sensors equipped with the coating provided herein can be subjected to conditions in which the sensors are soaked in a fluid other than ethanol.

In another aspect, the subject invention provides a method of continuously detecting the concentration of ethanol vapor in skin perspiration collected from a human subject, comprising:
  contacting a sample, the sample optionally comprising water vapor, with the sensing device provided herein;
  obtaining and storing the OCP of the sensor unit by scanning a first range of voltage across the sensor;

comparing the OCP to a threshold value characteristic to the material employed in the working electrode; and applying the OCP across the working and the reference electrodes while conducting a series of amperometric measurements;

wherein, if the OCP is less than the threshold value, the amperometric data are fitted against a pre-determined calibration curve to remove the signals arising from humidity in the surrounding environment and the concentration of ethanol is subsequently determined; and if the OCP is greater than the threshold value, the concentration of ethanol is directly determined based on the amperometric data.

In some embodiments, the sensing device is placed in direct contact with human skin. Monitoring the potential change in the anode with high accuracy is important for constructing a reliable ethanol sensor. Human skin comprises epidermis and dermis as the outermost two layers. Ethanol diffused out of the epidermis interacts with the anode of a fuel cell based sensor when the sensor is secured in close proximity to the skin surface.

In certain embodiments, the sensing device measures the concentration of ethanol in the presence of humidity by fitting the measured amperometric response against a pre-determined calibration curve. When the measured OCP is below a threshold value that is characteristic to the material employed as the electrode/catalyst, the potential, also known as $E_{cell}$, is stored as a bias voltage in the device. By applying the stored bias to the device during the amperometric measurement, the resulting current response is fitted against a pre-determined calibration curve stored in the device memory that corresponds with the specific bias voltage applied. The fitting of the calibration curve nullifies the signals produced by humidity, thus resulting in a more accurate measurement of the concentration of ethanol. In an exemplary embodiment, the threshold value to which the measured OCP is compared is about 0.35 V for a sensing device employing stainless steel as the electrode/catalyst material.

In yet another aspect, the subject invention provides a device for determining blood alcohol content (BAC) in a skin perspiration sample collected from a human subject, comprising:

the fuel cell based sensing device provided herein;
a means of displaying the ethanol concentration measured with the sensing device;
circuitry capable of processing and analyzing the ethanol concentration data output by the sensing device; and
optionally a casing that encloses the sensing device.

Figure 11:
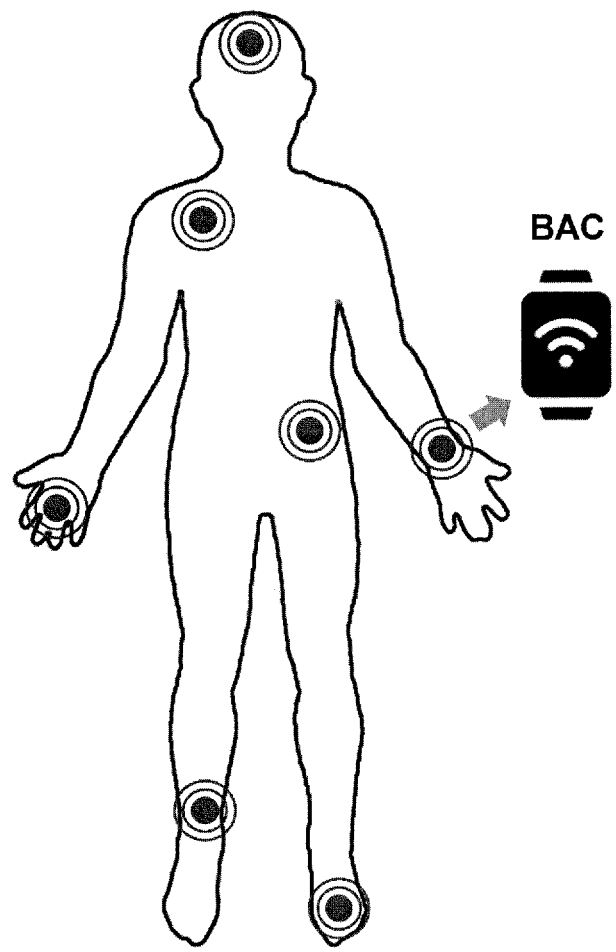
FIG. 11 shows the locations on a human body where an exemplary device housing the ethanol sensor can be mounted. The device outputs the BAC measurement of a human subject.

The ethanol sensing device provided herein can be integrated with additional components for various applications. Exemplary embodiments of the integrated device include, but are not limited to, wrist watches, bracelets, and arm bands; apparel such as shirts, jackets, and pants; accessories such as gloves, glasses, goggles, necklaces, and lanyards; headsets and headbands; shoes; vehicle accessories such as a steering wheel and its cover, a transmission stick and its cover, ignition button, and keys. In some embodiments, the measured BAC can be shown via a display capable of portraying data in the form of visual text and/or images. Non-limiting examples of the display include devices comprising liquid crystal materials, electrophoretic material, and/or electrochromic materials that are commonly found in applications such as electronic paper, computer monitors, handheld devices and the like. FIG. 11 shows the various locations on a human body where an embodiment of the wearable device can be mounted.

In some embodiments, the ethanol sensor provided herein can be incorporated (e.g., retrofitted) into devices manufactured by third parties.

In some embodiments, wearable devices can incorporate aesthetic designs such that the BAC can be monitored in a subject without the need for the subject to wear bulky electronic systems. In exemplary embodiments, the integrated sensing devices can help monitor a driver's BAC while he makes physical contact with the steering wheel, the transmission stick, or the ignition button to start the car. Advantageously, vehicle accessories incorporating ethanol sensor devices can potentially help lower the risk of DUI.

Embodiments of the integrated devices comprise casings for the ethanol sensors provided herein and can help prevent circuitry damage and hold the sensor components together. The materials that can be used to develop the casings include, but are not limited to, polymers, fabrics, and metals.

Figure 12A:
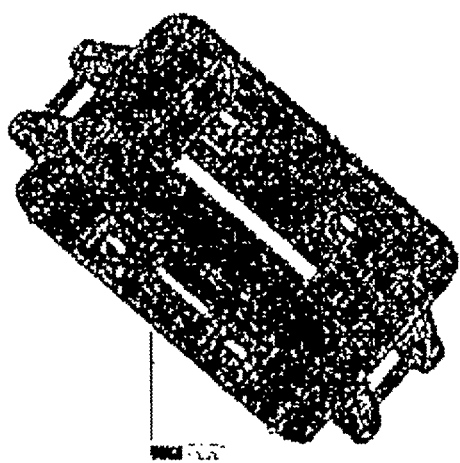
FIG. 12A is a depiction of the casing of the display, circuitry, and the sensor of an exemplary watch device.
Figure 12B:
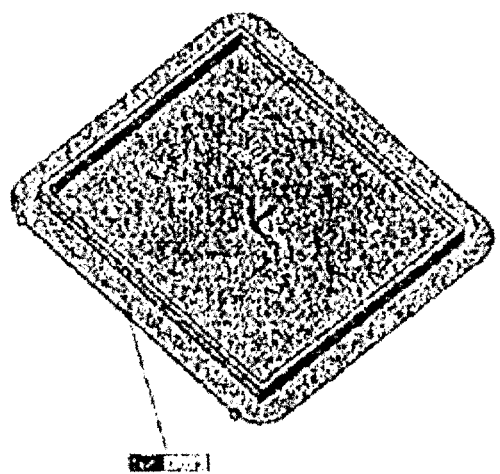
FIG. 12B is a depiction of the back cover of the casing shown in FIG. 12A of an exemplary watch device.
Figure 12C:
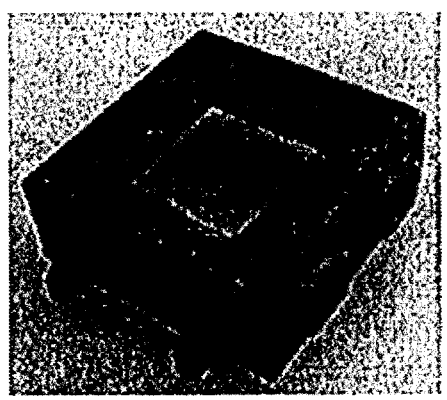
FIG. 12C shows the image of a 3D-printed watch device.

In an exemplary embodiment, an integrated sensing device in the form of a wrist watch can be developed using a 3D printing technique (FIG. 12C). The finished wrist watch device comprises a top casing (FIG. 12A) and bottom-cap casing (FIG. 12B), where the sensor, display, battery, and the circuitry can be enclosed inside the casing. In some embodiments, the development process can be expanded to molding techniques and any other technique available for plastic casing manufacturing.

In further embodiments, the integrated sensing device optionally comprises an electronic platform for receiving user input.

In addition to monitoring the concentration of ethanol vapor, technologies provided herein can also be used for sensors aimed to detect other chemical species capable of diffusing through the skin including, but not limited to, oxygen, carbon dioxide, carbon monoxide, acetone, glucose, salts, esters, aldehydes, and oxides of nitrogen. Also, certain blood species such as glucose, medicines and metabolites could be converted with a selected biological or chemical species to ethanol, which could then be sensed through the skin. Thus the integrated transdermal ethanol sensor provided herein could be used as a non-invasive indicator of blood levels of a variety of species, including glucose.

Further, in some embodiments, the transdermal fuel cell based ethanol sensor can be combined with other techniques including, but not limited to, ultrasound, electrotransport, and electroporation, that facilitate alcohol transport through the skin, leading to minimal or no delay in estimating the BAC based on the transdermal alcohol reading.

Advantageously, the fuel cell based sensor provided herein can monitor the concentration of ethanol vapor from skin perspiration and transdermal diffusion even in the presence of high humidity. This is accomplished by, in accordance with embodiments of the subject invention, taking advantage of low-cost materials such as stainless steel as the electrodes/catalysts. This combination of devices and techniques allows selectivity in detecting transdermal alcohol content and can be adapted in a variety of applications such as, for example, wearable devices.

EXAMPLES

The following are examples that illustrate the aforementioned embodiments and should not be construed as limiting. All of the chemical supplies provided herein, unless otherwise noted, were obtained via commercial sources and are readily available for procurement.

Example 1

NAFION® 424 reinforced with PTFE fiber in a thickness of approximately 0.03 cm was purchased from Sigma-Aldrich. The platinum-on-carbon catalyst (about 10 wt %) was purchased from Sigma-Aldrich. All other chemicals used were of analytical grade. Cyclic voltammetry (CV) and open circuit potential (OCP) measurements were performed using an analytical system Autolab potentiostat (Metrohm Autolab B.V., Netherlands). The scanning electron microscopy (SEM) and energy dispersive x-ray spectroscopy (EDX) results were obtained using a JEOL 6330F model SEM.

In the present example, two different types of fuel cell based sensors were constructed with platinum-on-carbon as the catalyst (ESU-1) and with stainless steel as the electrode and catalyst (ESU-2), respectively. The humidity was supplied on the transducer surface from a water bath at approximately 35° C., with $N_2$ as the carrier gas. Ethanol was introduced to the transducer surface by drop-cast method. The drop-cast method involves the casting of a known volume and concentration of ethanol using micropipette. All the measurements were carried out at 25° C.±2° C.

The active surface area of the working electrode was approximately 1.5 cm by 0.8 cm, while the active surface area of the counter electrode was slightly larger, about 1.5 cm by 1.0 cm, and the active surface of the reference electrode was about 1.5 cm by 0.2 cm. This design can effectively maximize the extent of oxygen reduction at the cathode, providing sufficient oxygen supply to consume the fuel at the anode/PEM interface.

ESU-1 and ESU-2 were each constructed by sandwiching 1 cm×1 cm of NAFION® membrane with a thickness of about 0.03 cm between the electrodes. The thickness of the MP stainless steel electrodes was approximately 0.02 cm. This was achieved by hot-pressing the sandwiched layers at approximately 79° C. with approximately 2500 PSI of pressure for about 10 min. For ESU-1, the working and reference electrodes comprised MP stainless steel, and the counter electrode comprised stainless steel coated with a platinum-on-carbon catalyst.

For ESU-2, all three electrodes comprised MP stainless steel without any platinum-on-carbon catalyst.

In contrast to the traditional fuel cell with an anode and a cathode, the fuel cell based sensor provided herein operates on a three-electrode system, in which the potential is measured between the working electrode, i.e., the anode, and the reference electrode, and the current is passed through the working electrode to the counter electrode, i.e., the cathode.

Example 2

Figure 2A:
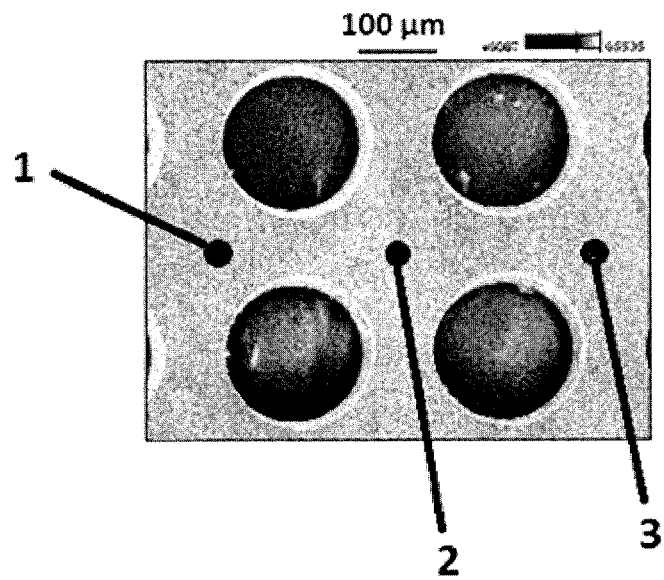
FIG. 2A is an SEM image of the stainless steel micro-perforated sheet. Spots 1, 2, and 3 indicate the points for EDX measurements.
Figure 2B:
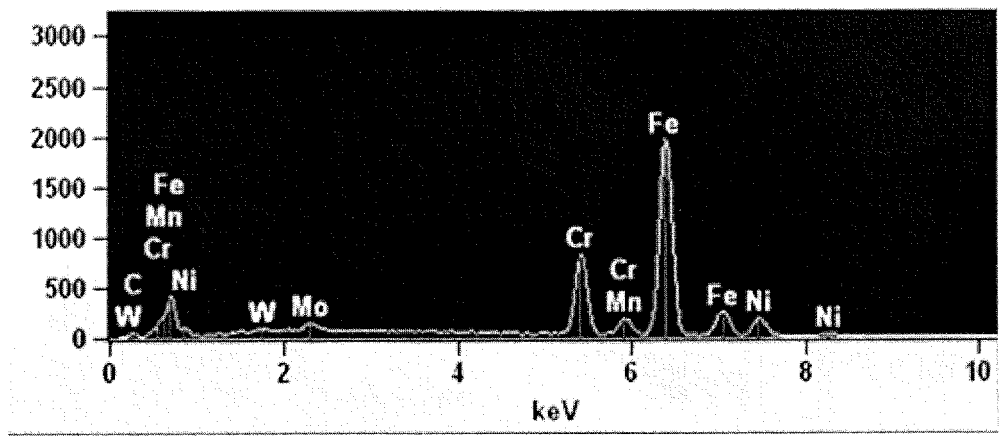
FIG. 2B is an EDX spectrum of the stainless steel micro-perforated sheet.

The MP stainless steel material used for the sensor construction was characterized using SEM and EDX. The pores were uniform in size with a diameter of approximately 180 μm and an inter-space distance of approximately 100 μm (FIG. 2A). For the EDX studies, the electron beam targeted three spots as marked in FIG. 2A. The resulting EDX spectrum (FIG. 2B) shows that the concentration of iron was higher than any other element present. This concentration of iron in the presence of chromium, nickel, manganese, and molybdenum is characteristic of a sample of stainless steel alloy. The composition calculation from the EDX data is given Table 1. Comparison between the compositions in Table 1 and the literature[11] indicates that the MP stainless steel used in this work was indeed 316/316L type stainless steel. The carbon content listed in Table 1 is higher compared to the theoretical composition in 316/316L stainless steel because it is difficult to eliminate all surface carbon contamination of the analyzed sample. Similarly, tungsten impurity was noticed in the results as well, though it existed in negligible amount.

Even though the 316/316L type stainless steel was used as an example for these studies, other stainless steel alloys, elemental metals, and carbon materials modified with nanomaterials can also be used for the fuel cell based ethanol sensor construction.

TABLE 1

Weight % data of micro-perforated stainless steel used in fuel cell based ethanol sensor.

|  | C | Cr | Mn | Fe | Ni | Mo | W |
|---|---|---|---|---|---|---|---|
| Spot 1 | 9.15 | 15.53 | 1.88 | 63.00 | 8.58 | 1.52 | 0.34 |
| Spot 2 | 9.28 | 15.70 | 1.67 | 63.39 | 8.44 | 1.51 | 0.00 |
| Spot 3 | 10.68 | 15.38 | 1.73 | 61.51 | 8.87 | 1.82 |  |

C Carbon;
Cr Chromium;
Mn Manganese;
Fe Iron;
Ni Nickel;
Mo Molybdenum;
W Tungsten.

Example 3

In addition to stainless steel, two different catalysts, gold and nickel, were studied. For both the gold and the nickel catalysts, the substrate material was stainless steel. Before the deposition of catalysts, the electrodes were ultra-sonicated for 10 min in isopropyl alcohol and then rinsed in water to remove any hydrocarbon residues. Gold catalyst was deposited on the electrodes by sputter coating at approximately 35 mbar of pressure and 30 mA of current. Each side of the electrodes was deposited with gold 10 times at about 50 seconds in duration. The nickel deposition involved several steps including acid cleaning, Wood's nickel strike, and Watt's nickel plating. The acid cleaning was achieved by using lead as the cathode and stainless steel as the anode. 98% of 205 mL of sulfuric acid is diluted with 1 L of water. Current at about 200 A/ft² in density was passed through the electrodes, which was kept below room temperature in an ice bath, for about 5 minutes after placing the electrodes in the solution using a galvanostatic supply. The base electrode was washed thoroughly in DI water and was subsequently dipped in an acid solution comprising sulfuric acid and hydrochloric acid (in the proportion of about 1:10:1000 respectively, 1000 mL being DI water) for about 30 to about 45 seconds.

The deposited catalysts were characterized by EDX. As shown in Table 2, the amount of nickel was found to be about 63.37%, while the composition of iron (from the stainless steel substrate) and carbon was approximately 3.49% and approximately 33.1%, respectively. From the EDX data it was identified that a thick layer of nickel was coated on the electrodes.

For the gold-coated electrodes (Table 3), the amount of gold was about 49.38%. In addition to gold, iron, nickel, and chromium were also found in the approximate amounts of 35.48%, 5.44% and 9.7%, respectively.

Studies showed that the deposition of a thin layer of metals directly on the membrane at an optimal thickness of about 5 to about 10 nm acts as catalyst for anodic and cathodic reactions. Methods used for the metal deposition on the membrane include, but are not limited to, sputtering, electron-beam coating, and thermal vapor deposition.

electrode catalyst and nickel as the counter and reference electrodes catalyst. This configuration provides the best ethanol oxidation reaction and oxygen reduction reaction in the fuel cell sensor with a higher reaction rate, which translates to higher output signal, sensitivity and linearity of the data range. This increase in the rate of the reaction also lowers the detection limit of the sensor. The $\Delta V$ between ethanol signal and humidity signal is also higher for stainless steel compared to the other electrodes, which again shows that by using stainless steel as the working electrode catalyst humidity interference can be reduced significantly.

Example 4

In the fuel cell setup, the ethanol gets oxidized at the anode and oxygen gets reduced at the cathode in the presence of humidity. Due to the fact that the formal potential ($E^{0'}$) of ethanol is much higher than the $E^{0'}$ of the catalyst,

TABLE 2

EDX spectrum analysis weight % data of micro-perforated nickel on base material stainless steel

| Element Line | Weight % | Weight % Error | Norm. Wt. % | Norm. Wt. % Err | Atom % | Atom % Error | Formula | Compnd % | Norm. Compnd % |
|---|---|---|---|---|---|---|---|---|---|
| C K | 33.14 | +/−3.92 | 33.14 | +/−3.92 | 70.73 | +/−8.36 | C | 33.14 | 33.14 |
| Fe K | 3.49 | +/−0.66 | 3.49 | +/−0.66 | 1.60 | +/−0.30 | Fe | 3.49 | 3.49 |
| Ni K | 63.37 | +/−1.85 | 63.37 | +/−1.85 | 27.67 | +/−0.81 | Ni | 63.37 | 63.37 |
| Total | 100.00 | | 100.00 | | 100.00 | | | 100.00 | 100.00 |

TABLE 3

EDX spectrum analysis weight % data of micro-perforated gold on base material stainless steel

| Element Line | Weight % | Weight % Error | Norm. Wt. % | Norm. Wt. % Err | Atom % | Atom % Error | Formula | Compnd % | Norm. Compnd % |
|---|---|---|---|---|---|---|---|---|---|
| Cr K | 9.70 | +/−0.63 | 9.70 | +/−0.63 | 16.01 | +/−1.04 | Cr | 9.70 | 9.70 |
| Fe K | 35.48 | +/−1.25 | 35.48 | +/−1.25 | 54.52 | +/−1.93 | Fe | 35.48 | 35.48 |
| Ni K | 5.44 | +/−0.57 | 5.44 | +/−0.57 | 7.96 | +/−0.84 | Ni | 5.44 | 5.44 |
| Au L | 49.38 | +/−4.13 | 49.38 | +/−4.13 | 21.52 | +/−1.80 | Au | 49.38 | 49.38 |
| Total | 100.00 | | 100.00 | | 100.00 | | | 100.00 | 100.00 |

The ethanol signal and the interfering humidity signal have been studied at the surface of stainless steel, gold, and nickel, respectively, using the OCP technique (FIG. 5). In ideal cases, the electro-catalytic activities of the catalyst materials should follow their respective value in the electromotive force (EMF) series; however, results provided herein show that the signals of oxygen reduction reaction were affected. For example, in FIG. 5, nickel has the lowest potential for ethanol oxidation signal compared to stainless steel and gold. This low signal was due to the fact that nickel prefers oxygen reduction reaction to ethanol oxidation when compared to stainless steel. Another way to explain this is that stainless steel reacts less with oxygen compared to nickel.

The values in FIG. 5 also show that the potential of ethanol oxidation and oxygen reduction are closer to their ideal values when stainless steel and nickel are employed as catalysts (ethanol oxidation at about 0.6 V, oxygen reduction reaction at about −0.2 V).

Figure 6A:
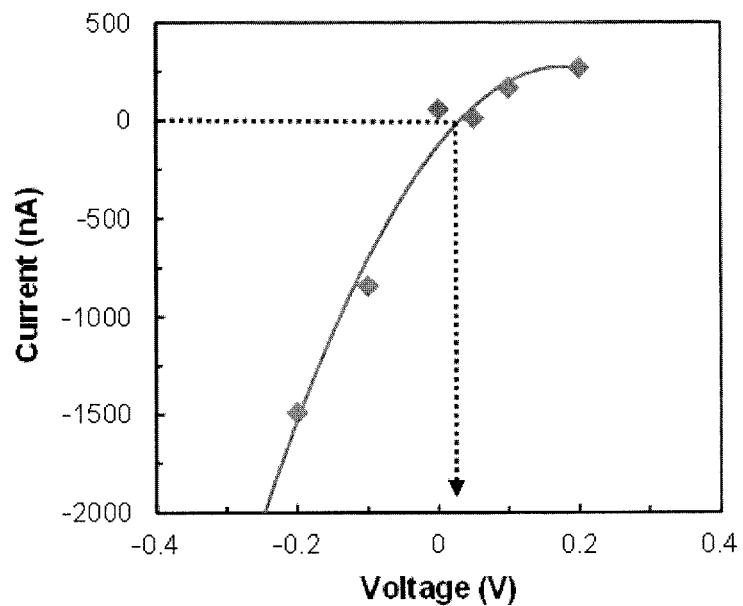
FIG. 6A demonstrates amperometric measurements of an exemplary fuel cell setup with stainless steel electrode at various applied potentials to obtain the $E_{cell}$ value for zero current in the presence of 50% humidity.
Figure 6B:
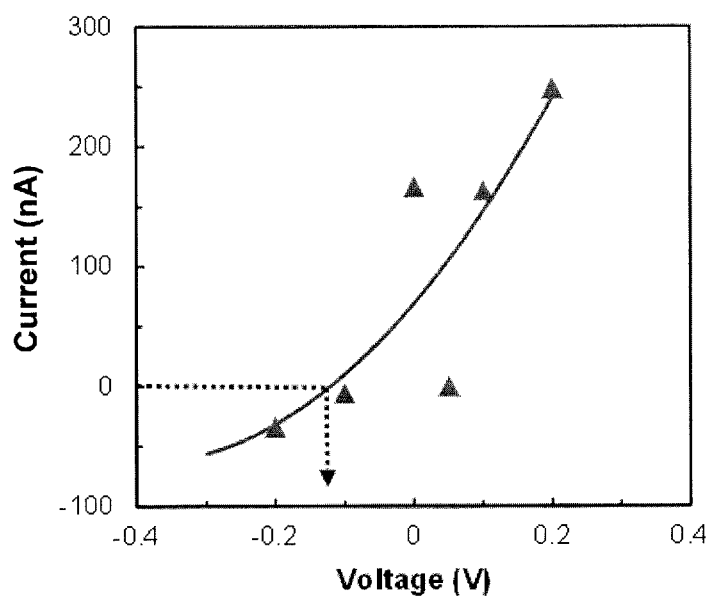
FIG. 6B demonstrates amperometric measurements of an exemplary fuel cell setup with gold electrode at various applied potentials to obtain the $E_{cell}$ value for zero current in the presence of 50% humidity.
Figure 6C:
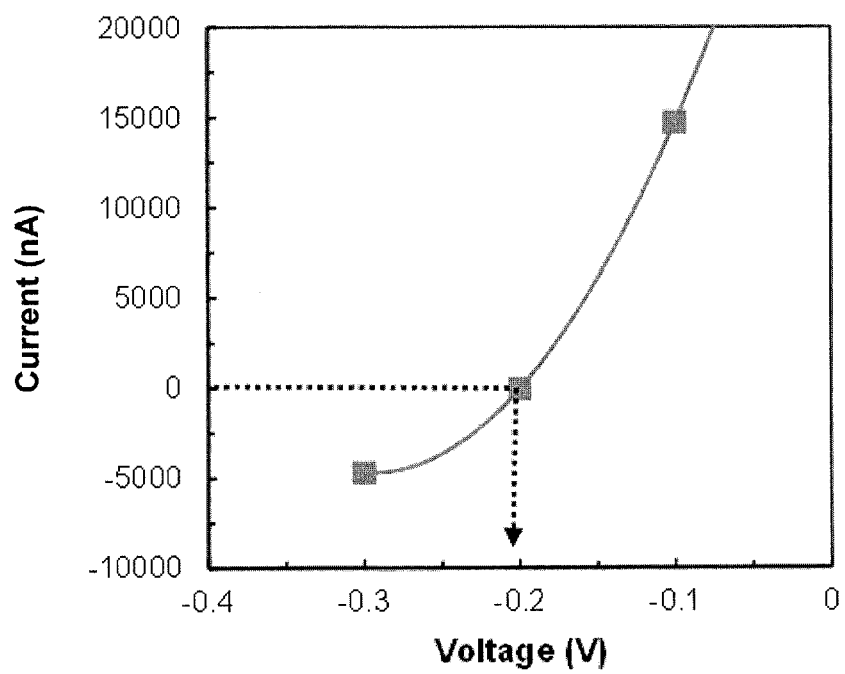
FIG. 6C demonstrates amperometric measurements of an exemplary fuel cell setup with nickel electrode at various applied potentials to obtain the $E_{cell}$ value for zero current in the presence of 50% humidity.

Based on these results, a preferred embodiment for an ethanol fuel cell sensor utilizes stainless steel as the working during amperometric measurements, where the applied potential is $E_{cell}$ and in the presence of ethanol, the current flows between the anode, i.e., the working electrode, and cathode, i.e., the counter electrode. To identify the $E_{cell}$ for each metal catalyst used, a series of amperometric measurements were made and the current was plotted vs. the applied potential at 50% humidity (FIG. 6).

The results show that the values of $E_{cell}$ depend on the type of catalyst used as well as the humidity level in the surrounding environment when a given catalyst is used.

The amount of humidity typically affects the $H^+$ ion transport through the membrane. The pH at the electrodes is solely controlled by the $H^+$ ion concentration. According to the Nernstian equation, potential is inversely proportional to pH. In high humidity, a greater number of $H^+$ ions are formed and transported through the membrane, which, in turn, increases the electrode potential and the $E_{cell}$. This increase in $H^+$ ion transfer also increases the amount of oxygen that gets reduced at the cathode and the amount of current produced.

Figure 7:
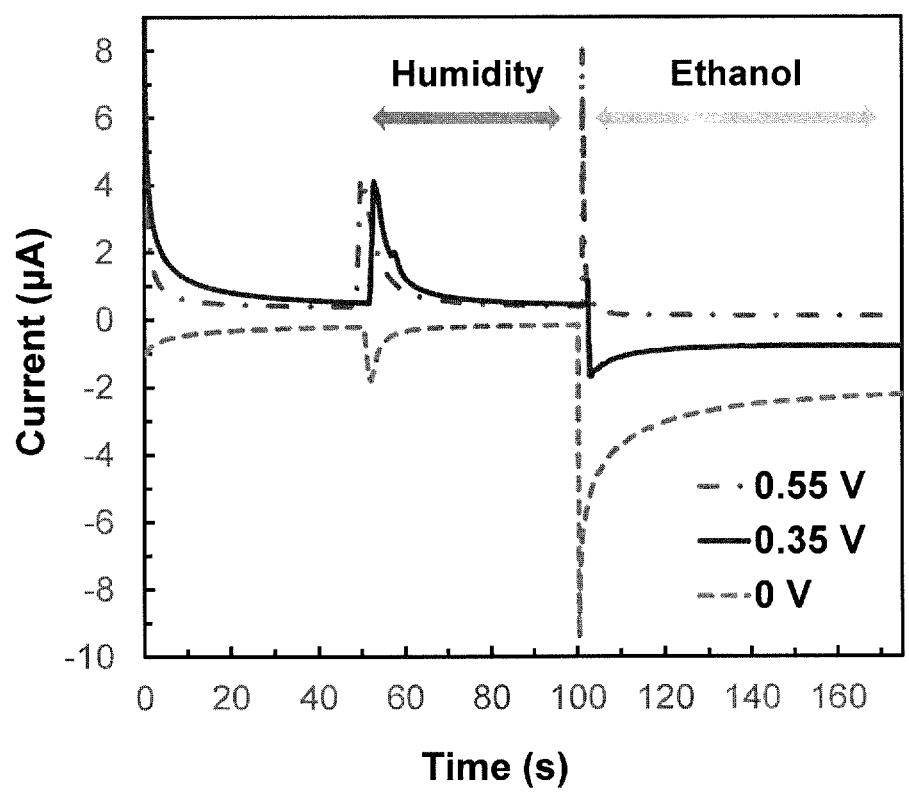
FIG. 7 shows the amperometric signals of an exemplary fuel cell sensor constructed with stainless steel at different applied potentials.

To demonstrate the reduction and elimination of a humidity signal, amperometric experiments were carried out at various potentials for stainless steel electrodes as shown in FIG. 7. In these experiments, humidity was introduced at 50 seconds and ethanol was introduced 50 seconds later. The potentials tested were 0, 0.35 and 0.55 V. As can be seen in FIG. 7, it is evident that there was a flip in polarization of the humidity signal if the applied potential was below the $E_{cell}$, which was at 0.15 V.

Figure 8:
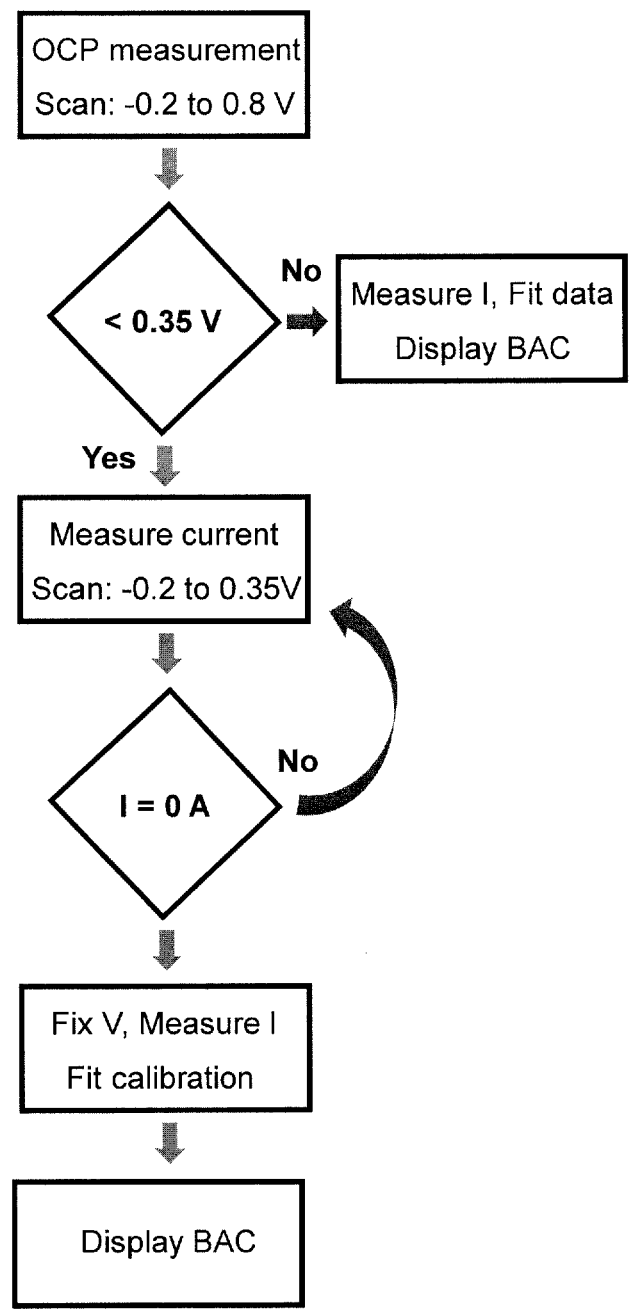
FIG. 8 is a flowchart representing ethanol sensing steps needed to obtain accurate BAC measurements by an exemplary fuel cell sensor employing stainless steel as the electrode material.

Based on these experimental observations, a flowchart (FIG. 8) was constructed to depict the process of measuring ethanol concentration using the fuel cell based sensor built in an exemplary device with appropriate circuitry and display components. The concept behind this flow chart involves the nullification of signal produced by humidity by a three-step process including: measuring the OCP of the sensor; if the OCP is below 0.35 V, scanning the applied potential to measure current, and determining the exact $E_{cell}$ value when the current is zero; and applying the exact $E_{cell}$ value across the sensor and measuring the current to fit an existing, pre-determined calibration curve. The final step is to display the BAC obtained from the calibration curve fit.

Example 5

Electrodes comprising stainless steel, gold, and nickel, respectively, have been studied using the amperometric technique to understand the effect of catalytic activity on ethanol oxidation current signal.

Figure 9A:
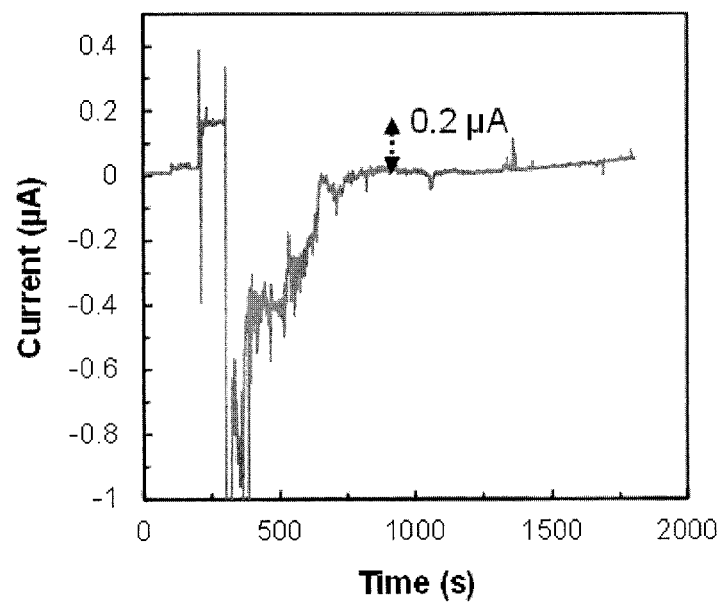
FIG. 9A shows the amperometric signals of 95% ethanol at an exemplary fuel cell sensor comprising stainless steel as the catalyst.
Figure 9B:
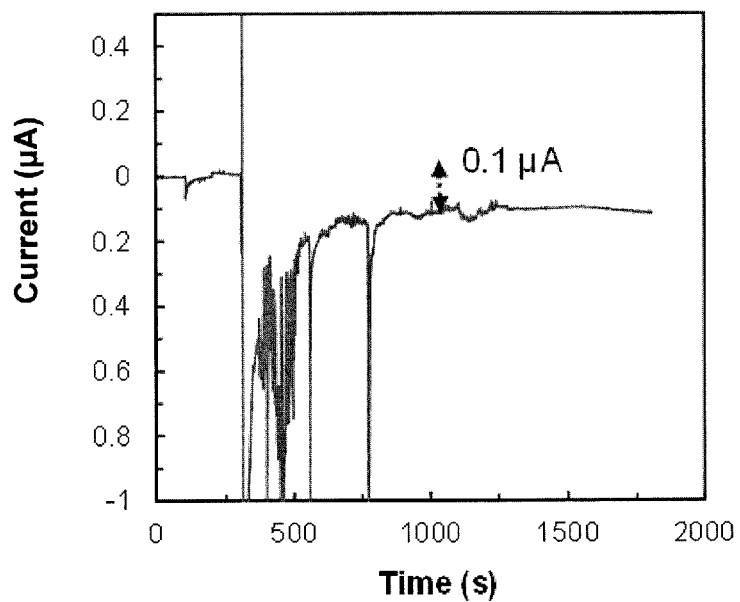
FIG. 9B shows the amperometric signals of 95% ethanol at an exemplary fuel cell sensor comprising gold as the catalyst.
Figure 9C:
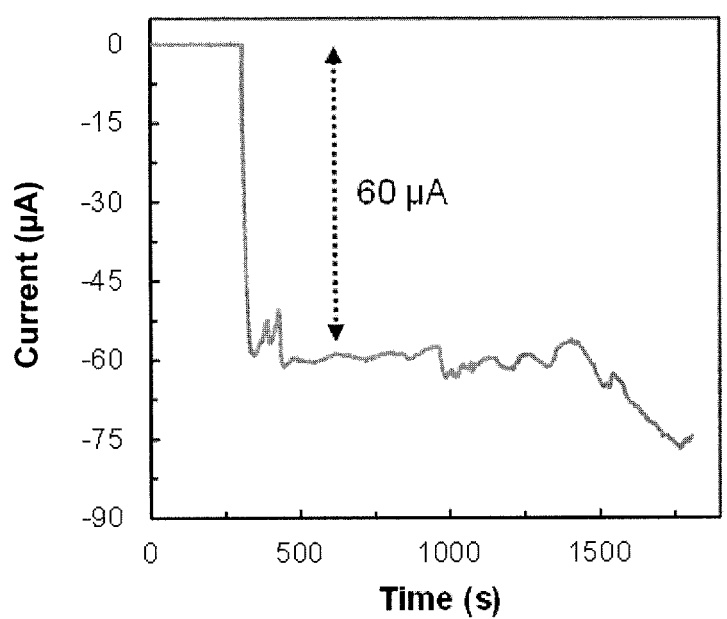
FIG. 9C shows the amperometric signals of 95% ethanol at an exemplary fuel cell sensor comprising nickel as the catalyst.

For these experiments, 95% ethanol was used to obtain the highest current possible. The amperometric results revealed that among these three catalysts, nickel provided the highest current (FIG. 9). This high current can be attributed to the high catalytic activity of nickel towards the oxygen reduction reaction, in which more than 3 electrons are transferred per oxygen molecule reduced. A higher rate of reduction leads to a higher amperometric current.

The current obtained in the stainless steel, gold, and nickel sensor was approximately 0.2 μA, approximately 0.1 μA, and approximately 60 μA, respectively. It is thus evident that the catalyst also plays an important role in determining the amperometric current.

Catalytic nanostructures comprising copper have also been studied. Copper nanoparticles were prepared using existing electrochemical deposition technique. These copper nanostructures also enhanced the ethanol oxidation current signal.

Example 6

Figure 10:
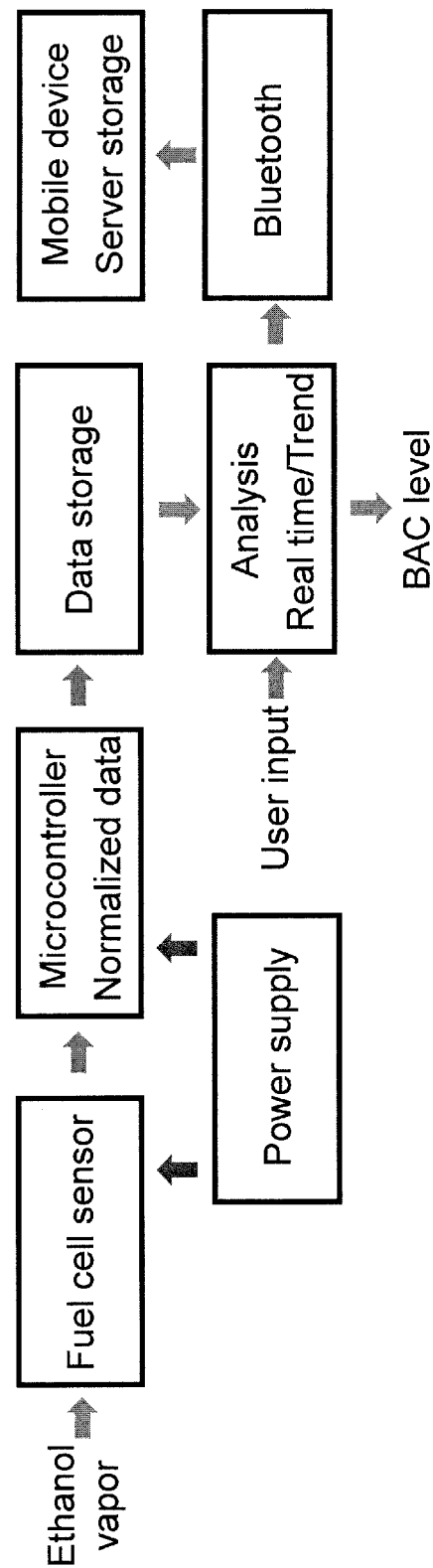
FIG. 10 is a flowchart representing the integration of the sensor and the backend circuit design along with each component's functions.

An exemplary integrated device enclosing an ethanol sensor provided herein operated from a 3.7 VDC lithium-Ion (Li-ion) battery capable of providing up to 1000 mAh. This voltage was regulated to provide a constant 3.3 VDC source to the system whose components and functions thereof are exemplified in FIG. 10 through a battery voltage in the range of 1.7 VDC≤$V_{DC}$≤3.7 VDC using a power management unit (TPS63030), which ensures a minimum battery life of approximately six months. The Li-ion battery can be recharged on the wearable platform through a micro-USB device connected directly to a Li-ion battery charging circuit which allows simultaneous system operation and charging functions.

The analog front end (AFE) sensing device (LMP91000) was chosen as the signal path solution between the microprocessor (MSP430F5529LP) and the ethanol fuel cell sensor due to its ability to detect current in the nanoampere (nA) range and provide an output voltage proportional to the fuel cell current times a gain factor. The AFE sensing device was fully configurable through software.

In order to ensure reliable AFE sensing operation and for calibration purposes, a digital-to-analog converter (DAC) was employed. The DAC (MCP4725) provided fully software-configurable reference voltage to the AFE sensing device of which a fixed percentage was applied across the ethanol fuel cell sensor for biasing purposes as determined during calibration time. The flow chart in FIG. 10 describes the various components and functions thereof in an embodiment of the fuel cell sensing device provided herein.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. C. L. Sanford, B. A. Mantooth, Determination of ethanol in alcohol samples using a modular raman spectrometer. *J. Chem. Educ.* 2001, 78, 1221-1224.
2. A. A. Shabaneh, S. H. Girei, P. T. Arasu, W. B. W. A. Rahman, A. A. A. Bakar, A. Z. Sadek, H. N. Lim, N. M. Huang, M. H. Yaaco, Reflectance response of tapered optical fiber coated with graphene oxide nanostructured thin film for aqueous ethanol sensing. *Optics Comm.* 2014, 331, 320-324.
3. T. K. An, H.-J. Yun, R. Narote, R. Kim, S. U. Lee, Y. Kim, S. Nam, H. Cha, Y. J. Jeong, K. Kim, S. Cho, S.-K. Kwon, Y.-H. Kim, C. E. Park, Synthesis and characterization of an ester-terminated organic semiconductor for ethanol vapor detection. *Org. Electronics* 2014, 15, 2277-2284.
4. Ming-Ru Yu, Gobalakrishnan Suyambrakasam, Ren-Jang Wu, Murthy Chavali, Performance evaluation of ZnO—CuO hetero junction solid state room temperature ethanol sensor. *Mat. Res. Bulletin* 2012, 47, 1713-1718.
5. R. A. Kadir, R. A. Rani, A. S. Zoolfakar, J. Z. Ou, M. Shafiei, W. Wlodarski, K. Kalantar-zadeh, Nb2O5 Schottky based ethanol vapour sensors: Effect of metallic catalysts. *Sens. Act. B: Chem.* 2014, 202, 74-82.
6. H.-J. Kim, J.-H. Lee, Highly sensitive and selective gas sensors using p-type oxide semiconductors: overview. *Sens. Act. B: Chem.* 2014, 192, 607-627.
7. K.-T. Jeng, W.-M. Huang, C.-C. Chien, N.-Y. Hsu, A versatile electrochemical fuel sensor for direct membrane fuel cell applications. *Sens. Act. B: Chem.* 2007, 125, 278-283.
8. L. Jiang, Z. Zhou, S. Wang, J. Liu, X. Zhao, G. Sun, Q. Xin, B. Zhou, Development of air-breathing direct ethanol fuel cells with PtSn as anode. *Prepr. Pap.-Am. Chem. Soc., Div. Fuel Chem.* 2004, 49, 668-670.

9. K.-C. Kim, S. M. Cho, H.-G. Choi, Detection of ethanol gas concentration by fuel cell sensors fabricated using a solid polymer electrolyte. *Sens. Act. B: Chem.* 2000, 67, 194-198.
10. J. C. Anderson, M. P. Hlastala, The kinetics of transdermal ethanol exchange. *J. Applied Physiology* 2006, 100, 649-655.
11. J. Izquierdo, L. Martín-Ruíz, B. M. Fernández-Pérez, L. Fernández-Mérida, J. J. Santana, R. M. Souto, Imaging local surface reactivity on stainless steels 304 and 316 in acid chloride solution using scanning electrochemical microscopy and the scanning vibrating electrode technique. *Electrochim. Acta* 2014, 134, 167-175.

We claim:

1. A fuel cell based sensing device for continuously detecting the concentration of ethanol vapor in a sample, comprising:
    a sensor unit comprising a working electrode as an anode, a counter electrode as a cathode, a reference electrode, and a polymer electrolyte membrane, the anode and the cathode being separated by, and respectively in electrical contact with, the polymer electrolyte membrane, the reference electrode being in electrical contact with the polymer electrolyte membrane and disposed adjacent to, though separated from, the counter electrode;
    circuitry capable of controlling the potential applied to the sensor unit; and
    circuitry capable of measuring the current output of the sensor unit;
    wherein the sensor unit is capable of separating signals produced by ethanol from those produced by background humidity.

2. The device according to claim 1, wherein the polymer electrolyte membrane is a proton exchange membrane (PEM).

3. The device according to claim 1, wherein the working electrode and the counter electrode each includes an active surface area, the active surface area of the working electrode being smaller than the active surface area of the counter electrode.

4. The device according to claim 1, wherein the sample is a product of a human transdermal diffusion process.

5. The device according to claim 4, the sample being skin perspiration.

6. The device according to claim 1, wherein the electrodes comprise a material selected from iron, gold, platinum, carbon, and one or more of these materials combined.

7. The device according to claim 6, wherein the working electrode comprises stainless steel.

8. The device according to claim 6, wherein each of the counter and the reference electrodes comprises nickel.

9. The device according to claim 1, further comprising a thin coating of ethanol-permeable membrane in electrical contact with the working electrode.

10. A method of continuously detecting the concentration of ethanol vapor in a skin perspiration sample collected from a human subject, the method comprising:
    contacting a sample, the sample optionally comprising water vapor, with a fuel cell based sensing device comprising a sensor unit comprising a working electrode as an anode, a counter electrode as a cathode, a reference electrode, and a polymer electrolyte membrane, the anode and the cathode being separated by, and respectively in electrical contact with, the electrolyte, the reference electrode being in electrical contact with the polymer electrolyte membrane and disposed adjacent to, though separated from, the counter electrode; circuitry capable of controlling the potential applied to the sensor unit; and circuitry capable of measuring the current output of the sensor unit, wherein the sensor unit is capable of separating signals produced by ethanol from those produced by background humidity, and wherein the electrodes comprise a material selected from iron, gold, platinum, carbon, and one or more of these materials combined;
    Obtaining and storing the open-circuit potential (OCP) of the sensor unit by scanning a first range of voltage across the sensor unit;
    comparing the OCP to a threshold value characteristic to the material employed in the working electrode; and
    applying the OCP across the working and the reference electrodes while conducting a series of amperometric measurements;
    wherein,
    if the OCP is less than the threshold value, the amperometric data are fitted against a pre-determined calibration curve to remove the signals arising from humidity in the surrounding environment and the concentration of ethanol is subsequently determined; and
    if the OCP is greater than the threshold value, the concentration of ethanol is directly determined based on the amperometric data.

11. The method according to claim 10, wherein the polymer electrolyte membrane is a proton exchange membrane (PEM).

12. The method according to claim 10, wherein the working electrode comprises stainless steel.

13. The method according to claim 10, wherein each of the counter and the reference electrodes comprises nickel.

14. The method according to claim 10, wherein the device is placed in direct contact with the skin surface of the subject.

15. The method according to claim 10, wherein the working electrode comprises stainless steel and each of the counter and reference electrodes comprises nickel.

16. A device for measuring blood alcohol content (BAC) in a skin perspiration sample collected from a human subject, comprising:
    a fuel cell based sensing device comprising a sensor unit comprising a working electrode as an anode, a counter electrode as a cathode, a reference electrode, and a polymer electrolyte membrane, the anode and the cathode being separated by, and respectively in electrical contact with, the polymer electrolyte membrane, the reference electrode being in electrical contact with the polymer electrolyte membrane and disposed adjacent to, though separated from, the counter electrode; circuitry capable of controlling the potential applied to the sensor unit; and circuitry capable of measuring the current output of the sensor unit, wherein the sensor unit is capable of separating signals produced by ethanol from those produced by background humidity, and wherein the electrodes comprise a material selected from iron, gold, platinum, carbon, and one or more of these materials combined;
    a means of displaying the ethanol concentration measured with the sensing device; and
    circuitry capable of processing and analyzing the ethanol concentration data output by the sensing device.

17. The device according to claim 16, further comprising an electronic platform coupled to the sensing device for receiving user input.

18. The device according to claim 16, comprising a casing for enclosing the sensing device, the casing being adapted to a format selected from wearable accessories, apparels, shoes, and vehicular accessories.

19. The device according to claim 16, comprising a power supply.

20. The device according to claim 16, wherein the working electrode comprises stainless steel and each of the counter and reference electrodes comprises nickel.

* * * * *